US012673158B2

(12) United States Patent
Comment et al.

(10) Patent No.: US 12,673,158 B2
(45) Date of Patent: Jul. 7, 2026

(54) SYSTEM AND METHOD FOR DRAWING A SOLUTION

(71) Applicant: GE Precision Healthcare LLC, Waukesha, WI (US)

(72) Inventors: Arnaud Comment, Cambridge (GB); Rui Chen, Clifton Park, NY (US); Albert Chen, Toronto (CA); Galen Reed, Dallas, TX (US); Jonathan Murray, Dousman, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/406,013

(22) Filed: Jan. 5, 2024

(65) Prior Publication Data

US 2024/0216607 A1     Jul. 4, 2024

Related U.S. Application Data

(62) Division of application No. 16/412,809, filed on May 15, 2019, now Pat. No. 11,925,786.

(51) Int. Cl.
A61M 5/165          (2006.01)
A61M 5/00           (2006.01)
          (Continued)

(52) U.S. Cl.
CPC ............ A61M 5/165 (2013.01); A61M 5/007 (2013.01); A61M 5/142 (2013.01);
          (Continued)

(58) Field of Classification Search
CPC ...... A61M 5/165; A61M 5/007; A61M 5/142; A61M 5/16877; A61M 5/31565; A61M 5/14212; A61M 5/16881; A61M 5/14216; A61M 5/1782; A61M 5/1456; A61M 5/31505; A61M 5/31593; A61M 5/16827; A61M 2005/3114; A61M 2005/3128; A61M 2202/0028; A61M 2202/0035; A61M 2202/0042; A61M 2205/125; A61M 2205/126; A61M 2205/75; A61M 2205/3324; A61M 2205/3327; A61M 2205/3368; A61M 2205/3306; A61M 2205/3393; A61M 39/223; A61M 39/22; A61M 39/24; A61M 2039/242; A61M 2039/2493; A61M 2039/0009; A61J 1/20;
          (Continued)

(56) References Cited

U.S. PATENT DOCUMENTS

2005/0238504 A1*  10/2005  Yajima .................. F04B 43/084
                                                          417/322
2012/0117985 A1*   5/2012  Urbahn .................. G01N 13/00
                                                          137/561 R
          (Continued)

*Primary Examiner* — Kevin C Sirmons
*Assistant Examiner* — Alexandra Lalonde

(57)          ABSTRACT

A method for drawing a solution using a system is provided. The system includes a filter, a vacuum source, and an actuator. The filter has an input port, a first output port, a second output port, and a flow path defined in part by the input port and the second output port. The vacuum source is in fluid communication with the first output port and operative to apply a vacuum to the flow path. The actuator is operative to facilitate movement of the solution along the flow path.

6 Claims, 5 Drawing Sheets

(51) Int. Cl.

| | |
|---|---|
| *A61M 5/142* | (2006.01) |
| *A61M 5/168* | (2006.01) |
| *A61M 5/315* | (2006.01) |
| *G01R 33/28* | (2006.01) |

(52) U.S. Cl.
CPC .... *A61M 5/16881* (2013.01); *A61M 5/31565* (2013.01); *G01R 33/282* (2013.01)

(58) Field of Classification Search
CPC ......... A61J 1/2003; A61J 1/2062; A61J 1/14; A61J 1/1475; A61J 1/2058; A61J 1/2096; A61J 1/1443; A61J 1/1456; A61J 1/2079; G01R 33/282; A61N 5/00; A61N 5/01; A61N 5/022; A61B 6/48; A61B 6/481; A61B 6/484; A61B 6/485; A61B 5/055
See application file for complete search history.

(56) References Cited

U.S. PATENT DOCUMENTS

| | | | |
|---|---|---|---|
| 2014/0012129 A1* | 1/2014 | Lohman ............. | G01R 33/5601 600/420 |
| 2015/0141943 A1* | 5/2015 | Koch ................... | A61M 1/782 604/320 |

* cited by examiner

SYSTEM AND METHOD FOR DRAWING A SOLUTION

CROSS REFERENCE TO RELATED APPLICATIONS

This application is a divisional of U.S. patent application Ser. No. 16/412,809, filed May 15, 2019, now U.S. Pat. No. 11,925,786, which application is herein incorporated by reference in its entirety.

BACKGROUND

Technical Field

Embodiments of the invention relate generally to hyperpolarized magnetic resonance imaging ("MRI") systems, and more specifically, to a system and method for drawing a solution.

Discussion of Art

MRI is a widely accepted and commercially available technique for obtaining digitized visual images representing the internal structure of objects having substantial populations of atomic nuclei that are susceptible to nuclear magnetic resonance ("NMR"). Many MRI systems use superconductive magnets to scan a subject/patient via imposing a strong main magnetic field on the nuclear spins in the subject to be imaged. The nuclear spins are excited by a radio frequency ("RF") signal/pulse transmitted by a RF coil at characteristics NMR (Larmor) frequencies. By spatially disturbing localized magnetic fields surrounding the subject and analyzing the resulting RF responses from the excited nuclear spins as they relax back to their equilibrium state, a map or image of the nuclear spins responses as a function of their spatial location is generated and displayed. An image of the nuclear spins responses provides a non-invasive view of a subject's internal structure.

In certain MRI procedures, referred to as Hyperpolarized MRI, e.g., Metabolic MRI, it is sometimes advantageous to inject a subject/patient with a hyperpolarized substance. The term "hyperpolarized," as used herein with respect to a substance, refers to a state of the substance in which the number of nuclear spins of the substance having a polarized state is greater than the number of nuclear spins of the substance having a polarized state at thermal equilibrium conditions. Due to the high percentage of nuclear spins having a polarized state, a hyperpolarized substance may generate an MR signal more than 10,000 times stronger than many non-hyperpolarized substances. Thus, many hyperpolarized substances are effective MRI tracers.

Methods of producing hyperpolarized substances often involve lowering the temperature of a substance in the presence of stable radicals within a strong magnetic field, and subsequently irradiating the substance and stable radicals with microwaves. As used herein, the term "stable radical" refers to an atom and/or molecule with a free electron that remains stable for an indefinite amount of time, and which is not readily removable from the substance in which it is dissolved without de-hyperpolarizing the substance. Following a Boltzmann distribution, the electron spins of the stable radicals become highly polarized at low temperatures within the strong magnetic field, and the microwaves transfer polarization from the stable radicals to the nuclear spins of the substance.

For example, Dynamic Nuclear Polarization ("DNP") with rapid dissolution is an efficient method of producing hyperpolarized substances that typically requires polarizing a sample mixture of molecules to be polarized and stable free radicals in a low temperature and high magnetic field environment. As the longitudinal relaxation time T1 of the nuclear spins of the solid-state sample at low field, i.e., outside of the polarizer, is very short, in the presence of the stable free radicals, the sample must be rapidly dissolved within the high magnetic field of the polarizer with hot solvent, e.g., water, and quickly transferred into a subject/patient for use in MRI.

As inferred above, many hyperpolarized substances created by such methods often have short life spans/lifetimes, i.e., the amount of time such substances are in a hyperpolarized state when in solution with other molecules, at physiological temperatures, e.g., 98.5° F., and/or when not in the presence of a strong magnetic field.

While approaches exist for drawing and delivering a dose of a hyperpolarized solution, i.e., a solution containing a hyperpolarized substance, into a patient, many such approaches usually require complex procedures and/or equipment, which in turn, usually requires quality control checks on an aliquot of the solution that is not representative of the true content of the solution to be injected into the patient. Moreover, many traditional systems for preparing and delivering a dose of a hyperpolarized solution into a patient include numerous moving mechanical parts, e.g., solenoids, and, as such, are usually costly to manufacture and/or maintain. Further, the local electromagnetic fields induced by solenoids or other moving mechanical parts can negatively alter the hyperpolarized solution, e.g., diminish its polarization. Many such traditional systems also have long draw times that reduce the portion of the lifetime of the injected hyperpolarized substance spent inside of a patient.

What is needed, therefore, is an improved system and method for drawing a solution.

BRIEF DESCRIPTION

In an embodiment a system for drawing a solution is provided. The system includes a filter, a vacuum source, and an actuator. The filter has an input port, a first output port, a second output port, and a flow path defined in part by the input port and the second output port. The vacuum source is in fluid communication with the first output port and operative to apply a vacuum to the flow path. The actuator is operative to facilitate movement of the solution along the flow path.

In another embodiment, a method for drawing a solution is provided. The method includes: applying a vacuum to a first output port of a filter; and moving, via an actuator, the solution along a flow path defined in part by an input port of the filter and a second output port of the filter.

In yet another embodiment, a system for drawing a solution is provided. The system includes a filter, a vacuum source, an actuator, a flow exchanger, a dispenser, a sensor, a normally open one-way check valve, and a normally closed one-way check valve. The filter has an input port, a first output port; a second output port, and a flow path defined in part by the input port and the second output port. The vacuum source is in fluid communication with the first output port and operative to apply a vacuum to the flow path. The actuator is operative to facilitate movement of the solution along the flow path. The flow exchanger has a first port, a second port and a third port. The first port is in fluid communication with the second output port of the filter. The dispenser is in fluid communication with the second port of the flow exchanger. The sensor is in fluid communication with the third port of the flow exchanger. The normally open one-way check valve is disposed between the second output port of the filter and the first port of the flow exchanger, and is operative to restrict flow of the solution from the flow exchanger to the second output port. The normally closed one-way check valve is disposed between the sensor and the third port of the flow exchanger and is operative to restrict flow of the solution from the sensor to the flow exchanger.

DRAWINGS

The present invention will be better understood from reading the following description of non-limiting embodiments, with reference to the attached drawings, wherein below:

DETAILED DESCRIPTION

Figure 1:
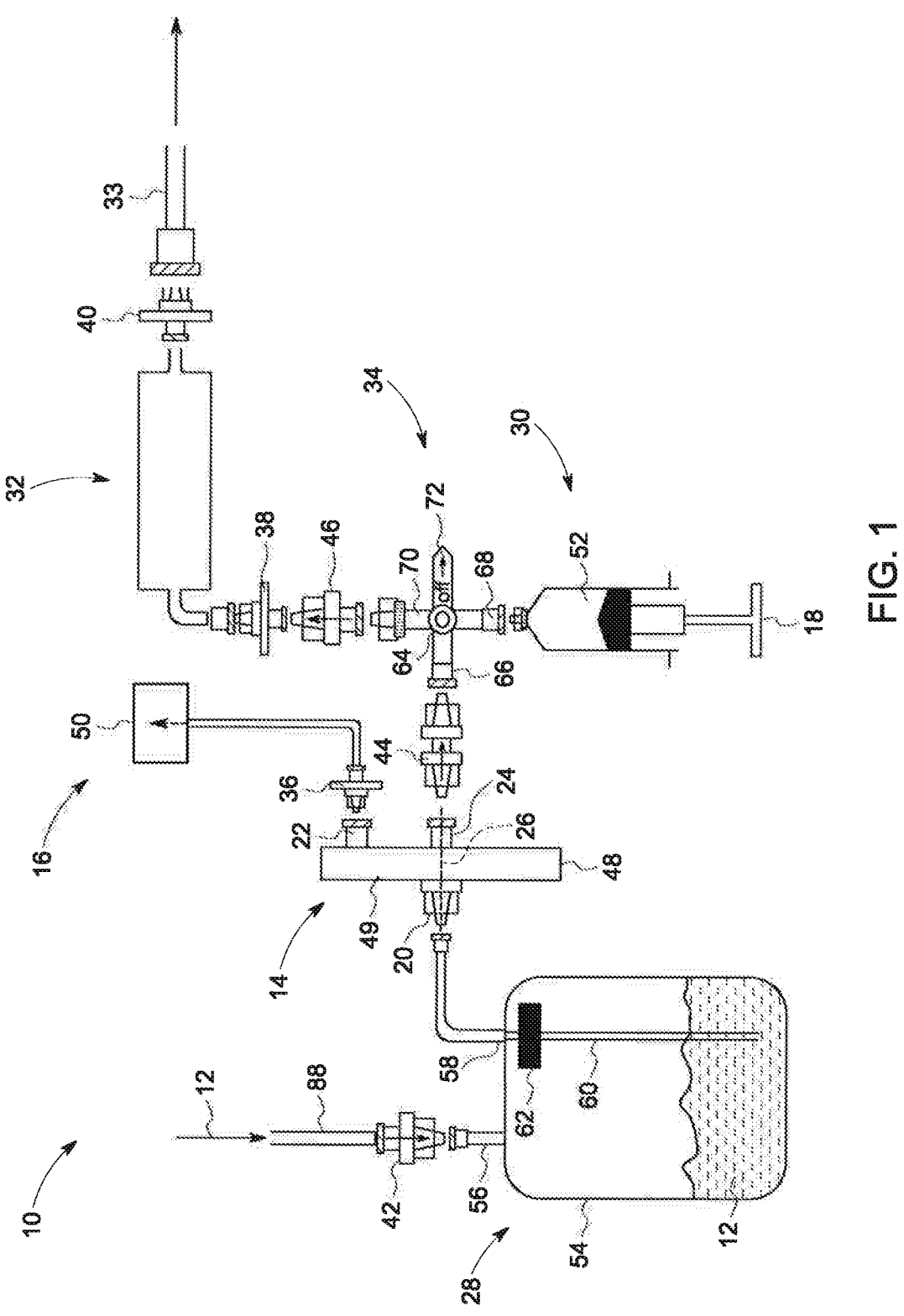
FIG. 1 is a schematic diagram of an exemplary system for drawing a solution, in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The terms "fluidly communicate", "fluid communication" and "communicate fluidly", as used herein, mean that a fluid, to include a gas, liquid and/or plasma, may flow from one referenced element to the other in at least one direction. The terms "upstream" and "downstream," as used herein, describe the position of the referenced elements with respect to a flow path of a gas, solid, liquid, and/or plasma flowing between and/or near the referenced elements.

Further, while the embodiments disclosed herein are described with respect to the drawing of a hyperpolarized solution for Hyperpolarized MRI, it is to be understood that embodiments of the present invention may be applicable to other systems and methods which utilize hyperpolarized substances and/or fluids, and/or other substances having short periods of usability that need to be prepared and/or drawn.

Referring now to FIG. 1, the major components of a system 10 for drawing a solution 12 is shown. The system 10 includes a filter 14, a vacuum source 16 and an actuator 18. The filter 14 has an input port 20, a first output port 22, a second output port 24 and a flow path (depicted as dashed line 26) defined in part by the input port 20 and the second output port 24. The vacuum source 16 is in fluid communication with the first output port 22 and operative to apply a vacuum to the flow path 26. The actuator 18 is operative to facilitate movement of the solution 12 along the flow path 26. As further shown in FIG. 1, in embodiments, the system 10 may also include a receiver vessel 28, a downstream device 30, a sensor 32, a flow exchanger 34, one or more additional filters 36, 38, 40, and/or one or more one-way check valves 42, 44, 46. As will be appreciated, the solution 12 may be a hyperpolarized substance such as water, alcohols, carboxylic acids (including keto acids), amino acids, alkanoic acids, fatty acids, dicarboxylic acids, tricarboxylic acids, alpha hydroxy acids (and derivatives thereof), sugars such as glucose, fructose and their derivatives, and urea, all of which may be enriched in carbon thirteen (13) ("$^{13}C$"), nitrogen fifteen ("$^{15}N$"), or deuterium ("$^{2}H$"), as well as any combination thereof.

The filter 14 has a body 48 with an internal space 49 which may include one or more membranes, filters or other devices through with flow path 26 passes. As stated above, the flow path 26 is defined in part by ports 20 and 24 and is exposed via port 22 to the vacuum generated by the vacuum source 16. In embodiments, the ports 24 and 22 may be arranged on the body 48 such that port 22 has a greater potential energy position than port 24, e.g., port 22 may be higher up than port 24 when the body 48 is placed on a horizontal surface. Thus, in embodiments, the force of gravity may influence the solution 12 to have a preference to flow from port 20 and out of port 24, as opposed to out of port 22. While FIG. 1 depicts the body 48 as being rectangular with ports 22 and 24 on separate ends of the body 48, it will be understood that, in embodiments, the body 48 may have other shapes, e.g., circular, square, triangular, oval, or any other suitable shape, with ports 22 and 24 being disposed at other locations on the body 48. As will be understood, the ports 20 and 24 may be simple openings, nozzles, nipples or any suitable type of device to allow the solution 12 to flow in and out of the body 48. Similarly, port 22 may be a nozzle, nipple or any suitable type of device to allow a pressure differential/gradient, e.g., a vacuum, to extend across the opening of the body 48 created by the port 22. In embodiments, the filter 14 may be a sterility assurance filter which filters out contaminants from the solution 12. Accordingly, the filter 14 may be operative to filter contaminants out of the solution 12 larger than about 0.2 micrometers ("microns").

The vacuum source 16 may include a body 50 housing a vacuum pump or other device capable of generating a vacuum. The body 50 may be fluidly connected to the first output port 22 of the filter 14 via a conduit/hose or other suitable device for applying extending the vacuum to the first input port 22.

The downstream device 30 is disposed downstream of the filter 14 and, in embodiments, may be a dispenser, i.e., a structure/body 52 operative to receive and contain the solution 12 and to dispense the solution. For example, in embodiments, the downstream device 30 may be a syringe. In such embodiments, the actuator 18 may be a plunger of the syringe as shown in FIG. 1. In other embodiments, the downstream device 30 may be a conduit, storage tank, beaker, flask, bottle, or any sterile or non-sterile container made out of plastic, glass, or metal suitable for storage and transport of aqueous solutions. In embodiments, the actuator 18 may be a vacuum pump, piston, or other type of device capable of moving the solution along the flow path 26 and/or from the downstream device 30 to the sensor 32.

The sensor 32 may be operative to obtain one or more readings/measurements of a property of the solution 12. In embodiments, the sensor 32 may be a measurement device, or other system/device/method to collect sample for measurement. For example, in embodiments, the sensor 32 may be a sterility sensor, an endotoxin sensor, a weight sensor, a volume sensor, a temperature sensor, a pH sensor, a conductivity sensor, a capacitive sensor, a magnetic sensor, a photo-sensitive sensor, an ultrasonic sensor, an optical sensor, and/or an NMR spectrometer. In embodiments, the sensor 32 may be operative to allow some and/or all of the portion, e.g., an aliquot, of the solution 12, received from the downstream device 30, to be removed and/or connected via conduit 33 for further testing and/or quality checks.

The receiver vessel 28 may have a body 54 operative to receive and contain the solution 12. The body 54 may have an input port 56 and an output port 58. The output port 58 may be fluidly connected to a conduit 60 operative to allow the solution 12 to flow out of the body 54. The conduit 60 may extend down into the body 54 from a position of high potential energy to a position of low potential energy, i.e., from the top to the bottom of the body 54. In embodiments, a filter 62 may be disposed in the conduit 60. As will be appreciated, in embodiments, the receiver vessel 28 may be operative to condition the solution 12, e.g., adjust the concentration, pH, osmolarity or other properties of the solution 12. In such embodiments, the body 54 may be preloaded with conditioning materials, e.g., neutralizers such as buffer solutions, NaOH or other basic compounds, HCl or other acidic compounds, EDTA, other necessary salt(s), as well as any combination thereof.

The flow exchanger 34 is operative to allow the solution 12 to flow from the second output port 24 of the filter 14 to the downstream device 30 and/or from the downstream device 30 to the sensor 32. Accordingly, in embodiments, the flow exchanger 34 has a body 64 with a first port 66, a second port 68 and a third port 70. The first port 66 fluidly communicates with the second output port 24 of the filter 14, the second port 68 fluidly communicates with the downstream device 30 and the third port 70 fluidly communicates with the sensor 32. While FIG. 1 depicts the body 64 as a three-way valve (indicated by lever 72), it will be understood that in embodiments, the body 64 may be a T-shaped conduit or other shape/device suitable to facilitate flow of the solution 12 as described herein, e.g., not a valve.

As yet further shown in FIG. 1, filter 36 may be disposed between the first output port 22 and the vacuum source 16 and may be operative to restrict flow/movement of the solution 12 out of the first output port 22. In other words, filter 36 allows the vacuum pressure to cross the first output port 22 but prevents and/or restricts movement of the solution 12 across the first output port 22. In embodiments, filter 36 may be a hydrophobic vent filter.

Filters 38 and 40 may be respectively disposed on opposite ends of the sensor 32. In embodiments, filters 38 and/or 40 may be hydrophilic vent filters.

Additionally, check valves 42, 44 and/or 46 may be disposable, which, as used herein, means that the valves 42, 44 and/or 46 may configured for single use, i.e., preparation of a single syringe 30 of solution for dispensing/injecting into a patient. Further, in embodiments, valves 42 and 44 may be normally opened and valve 46 may be normally closed.

Figure 2:
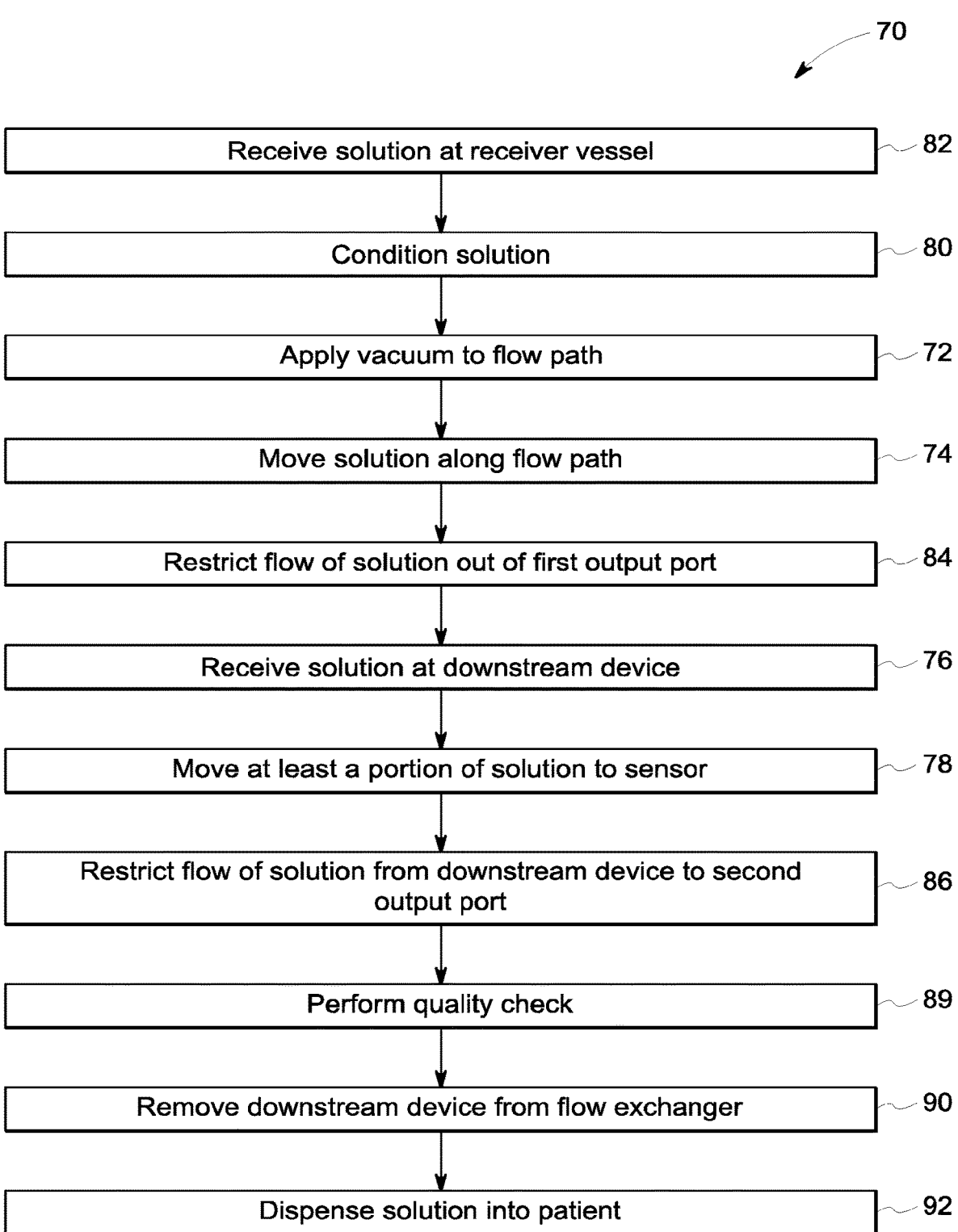
FIG. 2 is a flow chart depicting a method of drawing a solution utilizing the system of FIG. 1, in accordance with an embodiment of the present invention.

Referring now to FIG. 2, a method 70 for drawing a solution 12 utilizing the system 10 is shown. The method 70 includes applying 72 a vacuum to the first output port 22 and flow path 26 of the filter 14, and moving 74, via the actuator 18, the solution 12 along the flow path 26. In embodiments, the method 70 further includes receiving 76 the solution 12 at the downstream device 30, and moving 78 an aliquot (at least a portion) of the solution 12 from the downstream device 30 to the sensor 32. In embodiments, the method 70 may further include conditioning 80 the solution 12 via the receiver vessel 28 and/or receiving 82 the solution 12 in the receiver vessel 28. The method 70 may further include restricting 84 flow of the solution 12 out of the first output port 22 via the filter 36, and/or restricting 86 flow of the solution 12 from the downstream device 30 to the second output port 24 via check valve 44.

For example, referring to FIGS. 1 and 2, in an embodiment, the solution 12 may be received 82 at the receiver vessel 28 after flowing into the body 54 via a conduit 88. Flow of the solution 12 out of the body 54 may be restricted by check valve 42. Once in the body 54, the solution 12 may be conditioned 80 via neutralizing solutions to bring the solution's 12 pH within a range acceptable for injection into a patient. A syringe 30 may then be fluidly connected to the second port 68 of the flow exchanger 34 with the plunger 18 depressed into the body 52 of the syringe 30.

Figure 3:
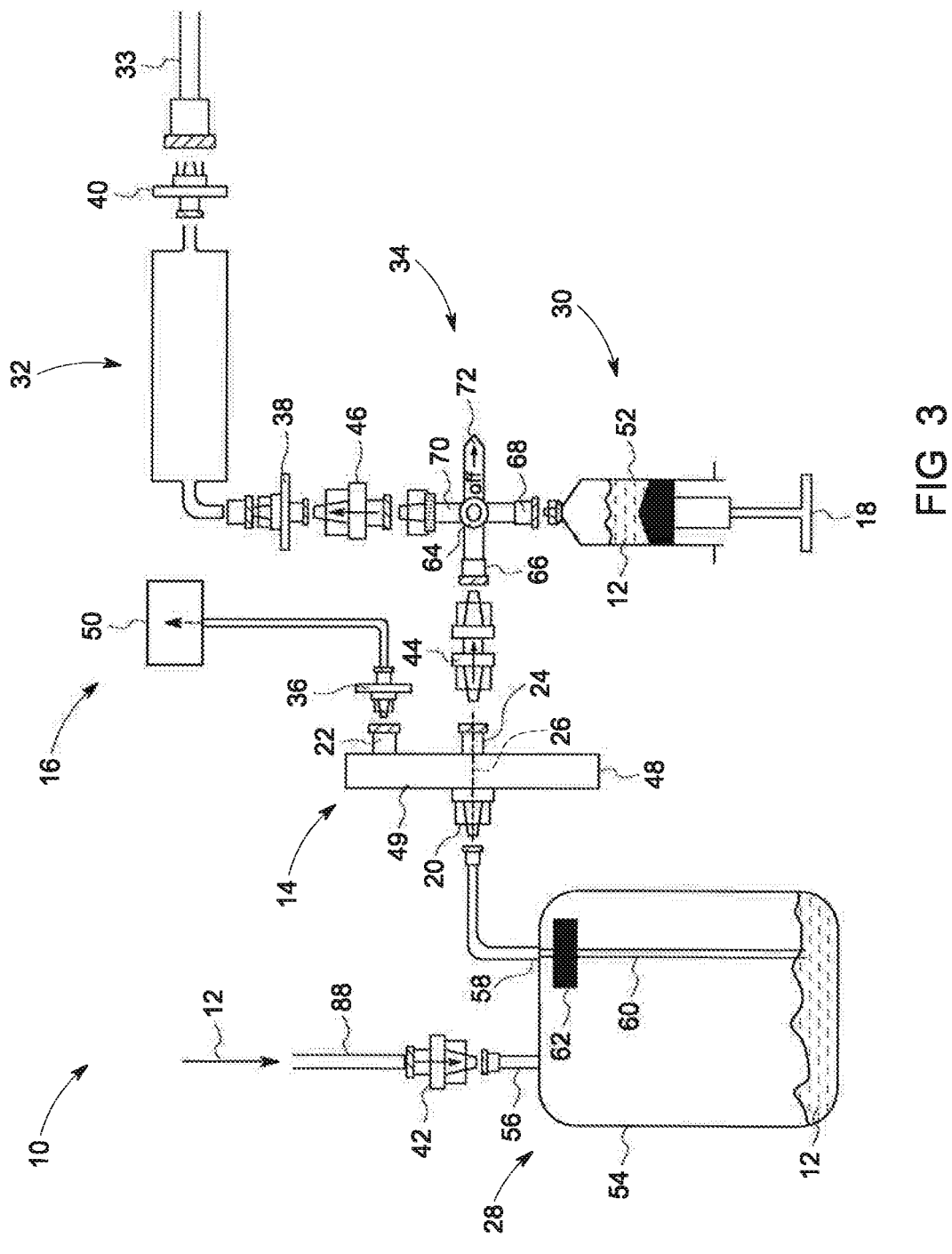
FIG. 3 is another schematic diagram of the system of FIG. 1, in accordance with an embodiment of the present invention.

Turning to FIGS. 2 and 3, a vacuum may be applied 72 via the vacuum source 16 to the flow path 26 such that excess air, i.e., "dead volume" is removed from the flow path 26. In embodiments, the vacuum may be applied at the same time or before the actuator/plunger 18 is actuated. The plunger 18 on the syringe 30 may then be actuated, i.e., extended out of the body 52, to create a vacuum pressure that causes the solution 12 to flow out of the receiver vessel 28 via conduit 60, into the filter 14 via input port 20, and into the body 52 of the syringe 30 via output port 24 and ports 66 and 68 of the flow exchanger 34.

Figure 4:
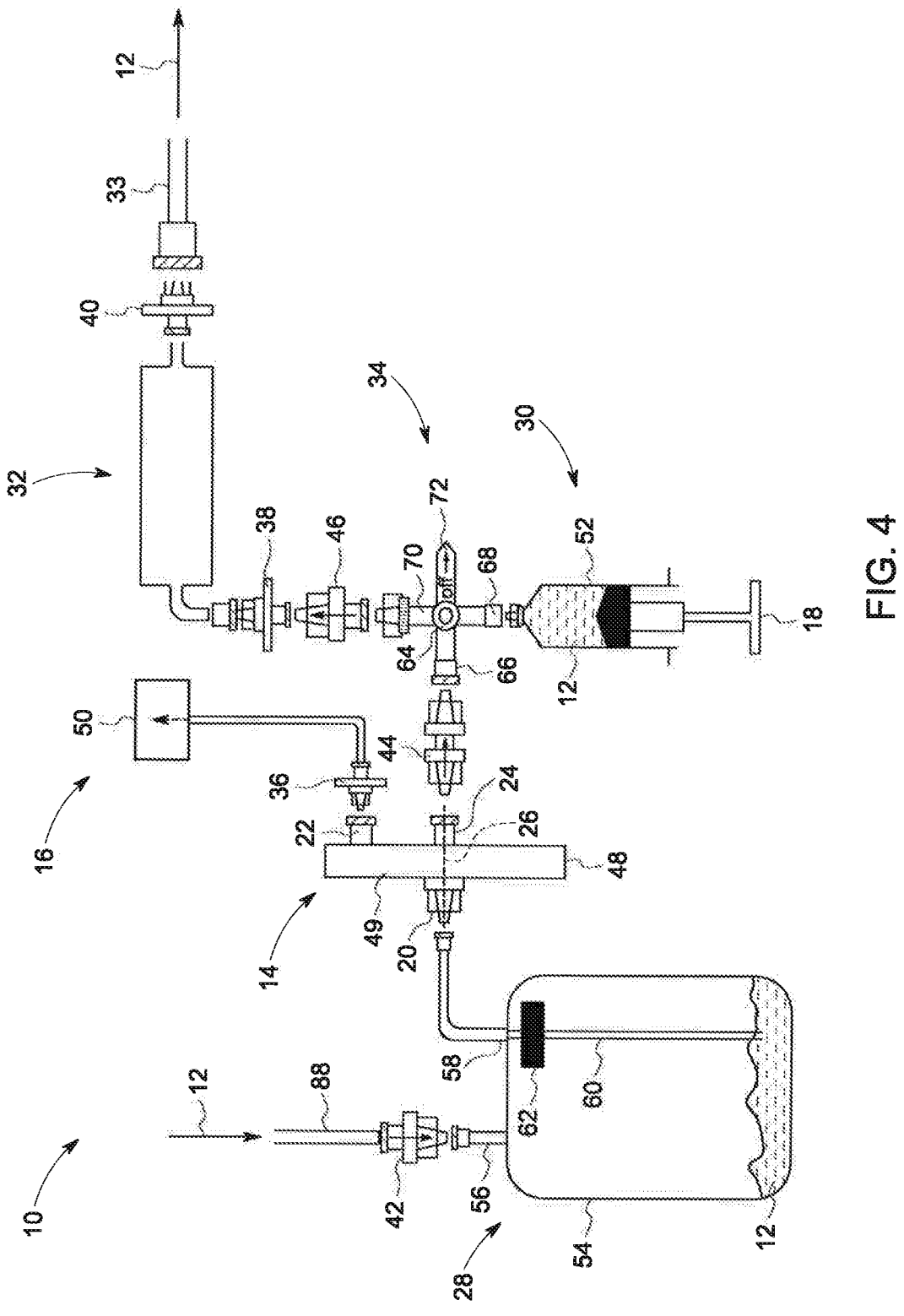
FIG. 4 is yet another schematic diagram of the system of FIG. 1, in accordance with an embodiment of the present invention.

As illustrated in FIGS. 2 and 4, the plunger 18 on the syringe 30 may then be actuated again, e.g., depressed into the body 52 of the syringe 30 such that an aliquot, i.e., a portion, of the solution 12 flows 78 out of the body 52 and to the sensor 32 via ports 68 and 70 of the flow exchanger 34, with check valve 44 restricting 86 flow of the solution 12 from the syringe 30 back to the filter 14.

Figure 5:
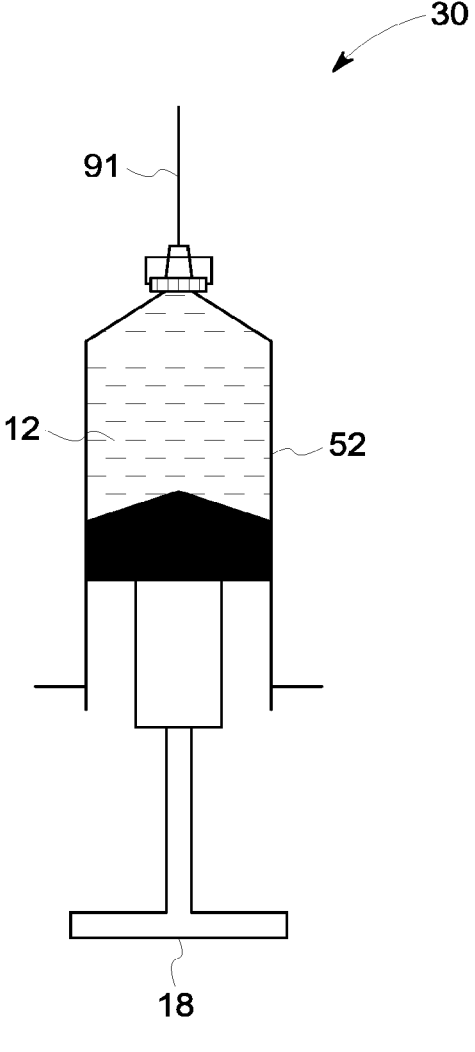
FIG. 5 is a schematic diagram of a dispenser of the system of FIG. 1, in accordance with an embodiment of the present invention.

The sensor 32 may then perform 89 one or more quality control checks as discussed above. Should the portion of the solution 12 be found to be acceptable, then the syringe 30 may be removed 90 (as shown in FIG. 5), and a needle 91, or an intravenous line, may then be added to the syringe 30 to facilitate dispensing 92, i.e., injection, of the solution 12 into a patient. The syringe 30 may also be placed on a power injector programmed to deliver specific amounts of the solution 12 at specific flow rates.

As will be appreciated, the filter 14, vacuum source 16, receiver vessel 12, downstream device 30, flow exchanger 34, sensor 32 and/or other components of the system 10 may be integrated into a larger structure which may be operative to be mobile, e.g., a support frame/chassis with wheels.

Finally, it is also to be understood that the system 10 may include the necessary electronics, software, memory, storage, databases, firmware, logic/state machines, microprocessors, communication links, displays or other visual or audio user interfaces, printing devices, and any other input/ output interfaces to perform the functions described herein and/or to achieve the results described herein. For example, the system 10 may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for drawing a solution is provided. The system includes a filter, a vacuum source, and an actuator. The filter has an input port, a first output port, a second output port, and a flow path defined in part by the input port and the second output port. The vacuum source is in fluid communication with the first output port and operative to apply a vacuum to the flow path. The actuator is operative to facilitate movement of the solution along the flow path. In certain embodiments, the system further includes a filter disposed between the first output port and the vacuum source and is operative to restrict flow of the solution from the filter to the vacuum source. In certain embodiments, the solution is hyperpolarized. In certain embodiments, the system further includes a receiver vessel in fluid communication with the input port and operative to condition the solution. In certain embodiments, the system further includes a dispenser operative to: fluidly communicate with the second output port; receive and contain the solution; and dispense the solution. In certain embodiments, the dispenser is a syringe and the actuator is a plunger of the syringe. In certain embodiments, the system further includes a sensor in fluid communication with the second output port and the dispenser and operative to obtain a measurement of at least a portion of the solution. In certain embodiments, the system further includes a normally open one-way check valve disposed between the second output port and a downstream device and operative to restrict flow of the solution from the downstream device to the second output port. In certain embodiments, the system further includes a normally closed one-way check valve, and a flow exchanger. The flow exchanger has: a first port in fluid communication with the normally open one-way check valve; a second port in fluid communication with the downstream device; and a third port in fluid communication with the normally closed one-way check valve.

Other embodiments provide for a method for drawing a solution. The method includes: applying a vacuum to a first output port of a filter; and moving, via an actuator, the solution along a flow path defined in part by an input port of the filter and a second output port of the filter. In certain embodiments, the method further includes receiving the solution at a dispenser in fluid communication with the second output port; and moving, via the actuator, at least a portion of the solution from the dispenser to a sensor. In certain embodiments, the dispenser is a syringe and the actuator is a plunger of the syringe. In certain embodiments, the method further includes restricting flow of the solution out of the first output port via a filter. In certain embodiments, the solution is hyperpolarized. In certain embodiments, the method further includes conditioning the solution via a receiver vessel in fluid communication with the input port. In certain embodiments, the method further includes restricting flow of the solution from a downstream device to the second output port via a one-way check valve.

Yet still other embodiments provide for a system for drawing a solution. The system includes a filter, a vacuum source, an actuator, a flow exchanger, a dispenser, a sensor, a normally open one-way check valve, and a normally closed one-way check valve. The filter has an input port, a first output port; a second output port, and a flow path defined in part by the input port and the second output port. The vacuum source is in fluid communication with the first output port and operative to apply a vacuum to the flow path. The actuator is operative to facilitate movement of the solution along the flow path. The flow exchanger has a first port, a second port and a third port. The first port is in fluid communication with the second output port of the filter. The dispenser is in fluid communication with the second port of the flow exchanger. The sensor is in fluid communication with the third port of the flow exchanger. The normally open one-way check valve is disposed between the second output port of the filter and the first port of the flow exchanger and is operative to restrict flow of the solution from the flow exchanger to the second output port. The normally closed one-way check valve is disposed between the sensor and the third port of the flow exchanger and is operative to restrict flow of the solution from the sensor to the flow exchanger. In certain embodiments, the system further includes a receiver vessel in fluid communication with the input port of the filter and operative to condition the solution. In certain embodiments, the dispenser is a syringe and the actuator is a plunger of the syringe. In certain embodiments, the system further includes a filter disposed between the first output port of the filter and the vacuum source and operative to restrict flow of the solution from the filter to the vacuum source.

Accordingly, by utilizing a series of one-way check valves, e.g., 42, 44, 46, in combination with a filter having a flow path with an applied vacuum, some embodiments of the present invention provide for a system for rapidly preparing and/or dispensing hyperpolarized substances without the need for actuated valves, e.g., solenoids. Thus, some embodiments of the present invention provide for a system for preparing and/or dispensing a hyperpolarized substance in a shorter amount of time, as compared to traditional systems/approaches, which in turn may result in a longer portion of the hyperpolarized substance's lifetime being spent within a patient. For example, some embodiments of the present invention may provide for 30-100 mL to be conditioned, quality checked and/or ready for dispensing/injection into a patient within 5-10 seconds.

Further, by providing for an aliquot of the solution 12 from the dispenser/syringe as the sample for quality control testing, some embodiments of the present invention may provide for better quality control over traditional systems which generally do not directly test the sample solution intended to be injected into a patient. Thus, some embodiments of the present invention mitigate issues related to mismatched parameters, e.g., f.i., concentrations, pH, etc., between a portion of the solution within a syringe intended to be injected into a patient, and a sample utilized for quality control checks.

Further still, by applying a vacuum to the flow path during the solution drawing method, as described above, some embodiments of the present invention reduce and/or mitigate the amount of dead volume within a dispenser/syringe, as compared to traditional approaches. As will be understood, the dead volume of a syringe is a volume of air sometimes found within a syringe after being filled with a solution for injection into a patient. As will be appreciated, the reduction and/or mitigation of dead volume in the syringe, in turn, results in a larger volume of solution within a dispenser/syringe being available for injection into a patient, which may assist in Hyperpolarizing MRI a large patient. Further, the reduction and/or mitigation of dead volume may also reduce a clinician's set up time as the need to eliminate air from a syringe prior to injection is reduced and/or eliminated. In addition, the existence of large air space in a syringe may slow down the transfer speed of solution from receiver through filter. By eliminating or minimizing the dead volume air, the transfer speed of hyperpolarized solution may be higher.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined in part by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

The invention claimed is:

1. A method for drawing a solution, the method comprising:

applying a vacuum to a first output port (22) of a filter (14);

moving, via an actuator (18), the solution along a flow path (26) defined in part by an input port (20) of the filter and a second output port (24) of the filter;

restricting flow of the solution from a downstream device (30) to the second output port via a one-way check valve (44);

operating the actuator in conjunction with a flow exchanger (34) to selectively direct the solution from the downstream device to a sensor (32) for quality control checks before dispensing;

wherein the flow exchanger comprises:

a first port (66) in fluid communication with the one-way check valve;

a second port (68) in fluid communication with and directly coupled to the downstream device;

a third port (70) in fluid communication with a normally closed one-way check valve (46), wherein the normally closed one-way check valve is disposed between the sensor and the third port; and wherein the one-way check valve (44) is directly coupled to the second output port (24) and the first port (66).

2. The method of claim 1 further comprising:

receiving the solution at a dispenser in fluid communication with the second output port.

3. The method of claim 2, wherein the dispenser is a syringe and the actuator is a plunger of the syringe.

4. The method of claim 1 further comprising:

restricting flow of the solution out of the first output port via a second filter (36).

5. The method of claim 1, wherein the solution is hyperpolarized.

6. The method of claim 1 further comprising:

conditioning the solution via a receiver vessel in fluid communication with the input port.

\* \* \* \* \*